(12) United States Patent
Piccirillo

(10) Patent No.: US 6,284,139 B1
(45) Date of Patent: Sep. 4, 2001

(54) PERITONEAL DIALYSIS METHOD

(76) Inventor: Vito Piccirillo, 6153 W. 64th St., Chicago, IL (US) 60638

( * ) Notice: Subject to any disclaimer, the term of this patent is extended or adjusted under 35 U.S.C. 154(b) by 0 days.

(21) Appl. No.: 08/624,872

(22) Filed: Mar. 27, 1996

(51) Int. Cl.[7] .................................................. A61M 1/28
(52) U.S. Cl. ............................ 210/645; 210/646; 604/29
(58) Field of Search ................................. 210/241, 321.6, 210/321.71, 645, 321.72, 646; 280/32.6, 35, 47.35, 79.3, 651; 312/107, 108, 111, 201, 209, 249.1, 249.8, 308; 604/29

(56) References Cited

U.S. PATENT DOCUMENTS

| | | | |
|---|---|---|---|
| 3,529,363 | * | 9/1970 | Versaci ............................... 210/321.3 |
| 3,730,601 | * | 5/1973 | Misenheimer, III ................. 312/108 |
| 3,868,154 | * | 2/1975 | Macdonald et al. ................. 312/209 |
| 4,585,436 | * | 4/1986 | Davis et al. .......................... 604/29 |
| 4,681,378 | * | 7/1987 | Hellman, III ........................ 312/107 |
| 4,682,750 | * | 7/1987 | Rudolph et al. ..................... 280/32.5 |
| 4,895,380 | * | 1/1990 | Brooks et al. ....................... 280/32.6 |
| 4,923,202 | * | 5/1990 | Breveglieri et al. ............... 280/47.35 |
| 4,998,023 | * | 3/1991 | Kitts .................................... 312/108 |
| 5,330,064 | * | 7/1994 | Hall ..................................... 280/79.3 |
| 5,492,399 | * | 2/1996 | Tillack ................................ 312/111 |
| 5,531,464 | * | 7/1996 | Maurer et al. ...................... 280/79.3 |

FOREIGN PATENT DOCUMENTS

WO 95/20985 * 8/1995 (WO).

OTHER PUBLICATIONS

Polish Tech. Rev., vol. 113, No. 1, p. 19 (1979).*

* cited by examiner

*Primary Examiner*—John Kim
(74) *Attorney, Agent, or Firm*—Wood, Phillips, VanSanten, Clark & Mortimer

(57) ABSTRACT

A portable dialysis system has a self-contained dialysis unit and a support for the dialysis unit to maintain the dialysis unit in an elevated position relative to a subjacent surface. The support has a length, a width, and a height, with the height of the support not exceeding four feet, the width of the support not exceeding three feet, and the length of the support not exceeding four feet. The unit is provided on a support, with there being structure on the support for facilitating movement of the support with the dialysis unit in the operative position thereon relative to the subjacent surface.

4 Claims, 3 Drawing Sheets

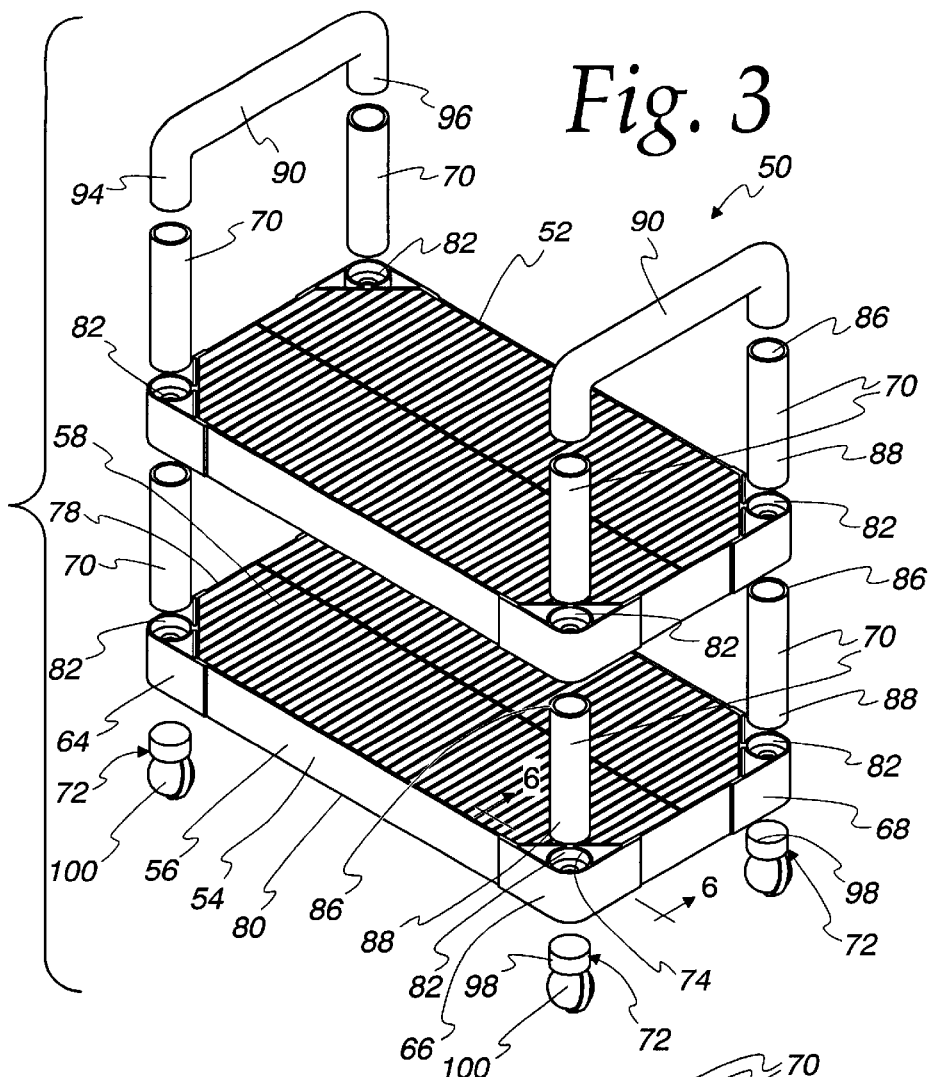

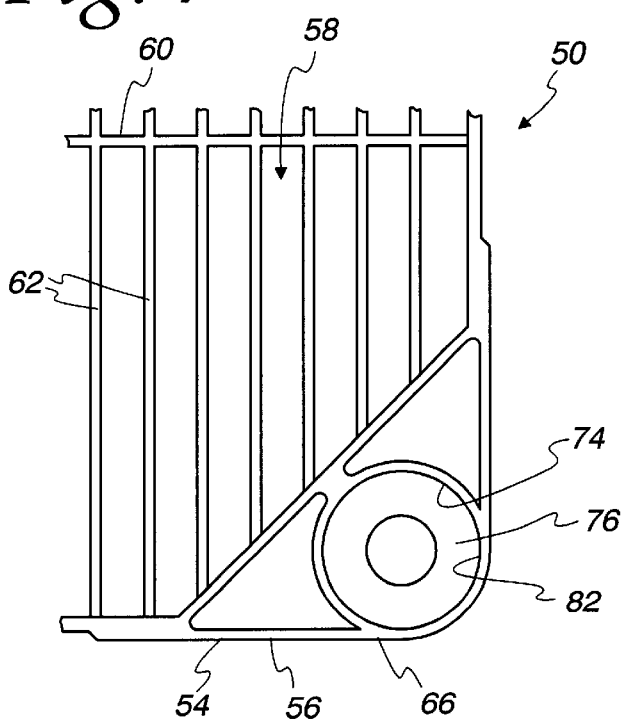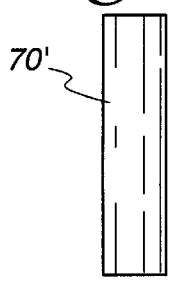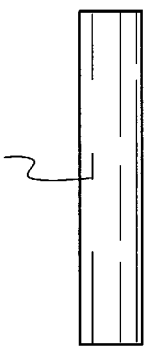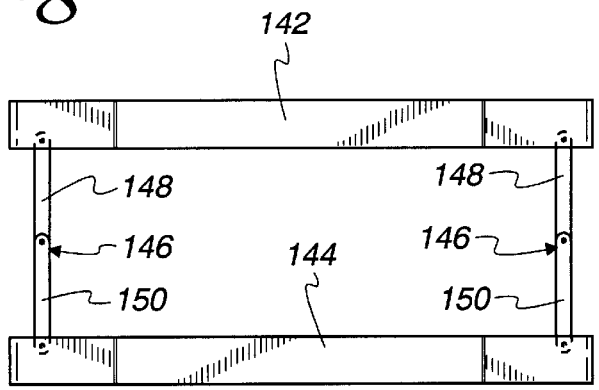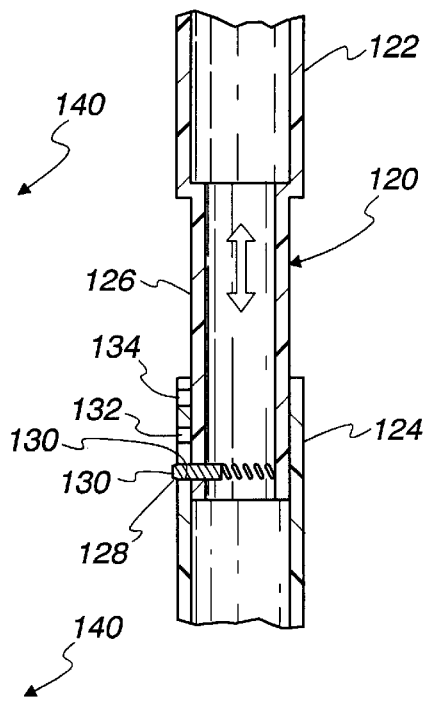

PERITONEAL DIALYSIS METHOD

BACKGROUND OF THE INVENTION

1. Field of the Invention

This invention relates to dialysis and, more particularly, to a system, including equipment for performing dialysis and a support for the dialysis equipment which can be conveniently moved by a patient during the dialysis procedure. The invention also relates to a support that is collapsible to facilitate its transportation.

2. Background Art

Patients suffering from terminal renal failure can be saved only by ongoing dialysis treatment or kidney transplantation. Until recently, patients had to travel to a dedicated dialysis center for treatment. The patient was confirmed to a single location during the entire procedure, which could proceed for up to ten hours.

Baxter Health Care Corporation's recent development of a compact dialysis system has allowed the dialysis procedure to take place at virtually any location. This system, identified as a "continuous ambulatory peritoneal dialysis" system (CAPD system), is reduced significantly in size over earlier systems. The basic system consists of a relatively small control unit and a reservoir to permit circulation of fluids into the patient and removal of fluids from the patient during the dialysis procedure.

While the CAPD systems have made dialysis treatment considerably more convenient to the patient, the patient nonetheless has generally been confirmed to a single location throughout the procedure. Typically, the patient will remain in a bed or chair through the entire procedure, with mobility limited to a very small range as permitted by the connections between the equipment and the patient.

To accommodate the CAPD system, the patient may custom design a fixed support system in close proximity to his/her bed or chair. While it is desirable for the patient to move around during the procedure, the absence of a portable support for the CAPD system makes this impractical. Thus, patients may, for all practical purposes, be confined to one location throughout the treatment. This is an obvious inconvenience to a patient and in most cases precludes travel by the patient for any extended length of time away from the location that has been adapted to the CAPD system. As a result, the lifestyle of most patients needing regular dialysis treatment becomes drastically altered.

SUMMARY OF THE INVENTION

It is an objective of the present invention to overcome one or more of the problems, identified above.

In one form of the invention, a portable dialysis system is provided having a self-contained dialysis unit and a support for the dialysis unit to maintain the dialysis unit in an elevated position relative to a subjacent surface. The support has a length, a width, and a height, with the height of the support not exceeding four feet, the width of the support not exceeding three feet, and the length of the support not exceeding four feet. The unit is provided on a support, with there being structure on the support for facilitating movement of the support, with the dialysis unit in the operative position thereon, relative to the subjacent surface.

In one form, the structure for facilitating movement of the support is a plurality of wheels.

In one form, the support includes at least first and second structural elements and structure cooperating between the first and second structural elements for allowing the first and second structural elements to be repositioned relative to each other to thereby allow the support to be selectively changed between assembled and collapsed states without the use of separate fasteners.

In one form, there are a plurality of structural elements that define the entire support and structure cooperating between the plurality of structural elements to allow the plurality of structural elements to be repositioned relative to each other to thereby allow the support to be selectively changed between assembled and collapsed states without the use of separate fasteners.

There may be at least six structural elements in the plurality of structural elements.

In one form, the support has a perimeter volume in each of the assembled and collapsed states and the perimeter volume of the support in the collapsed state is no more than one-third the perimeter volume of the support in the assembled state.

The structure cooperating between the plurality of structural elements may allow the plurality of structural elements to be press fit together.

In one form, the support is made entirely from plastic.

The support may be defined by at least six structural elements, with there being structure cooperating between the at least six structural elements for allowing the six structural elements to be repositioned relative to each other to thereby allow the support to be selectively changed between assembled and collapsed states.

In one form, the support includes at least first and second spaced shelves and an upright extending between the shelves so as to maintain a predetermined space therebetween. The upright has a length and is defined by first and second parts which can be selectively maintained in a plurality of different positions corresponding to different lengths for the upright.

In another form of the invention, a portable dialysis system is provided including a dialysis unit and a support to maintain the dialysis unit in an elevated, operative position relative to a subjacent surface. The support has a plurality of structural elements that are repositionable relative to each other to thereby place the support selectively in an assembled state and a collapsed state. The support has a perimeter volume in each of the assembled and collapsed states, with the perimeter volume of the support in the collapsed state being no more than one-third the perimeter volume of the support in the assembled state.

In one form, there are at least six structural elements defining the support, including at least two flat shelves and at least one upright extending between the shelves.

The six structural elements may be fully separable, each from the other, with the support in the collapsed state.

In still another form of the invention, a portable dialysis system is provided having a dialysis unit and a support for the dialysis unit to maintain the dialysis unit in an elevated, operative position relative to a subjacent surface. The support has a plurality of structural elements with structure cooperating between the plurality of structural elements for allowing the plurality of structural elements to be repositioned relative to each other to thereby change the support selectively between an assembled state and a collapsed state without the use of separate fasteners.

BRIEF DESCRIPTION OF THE DRAWINGS

FIG. 3 is an exploded, perspective view of a modified form of support for a dialysis system, according to the present invention;

FIG. 4 is a perspective view of the support in FIG. 3 in a collapsed state;

FIG. 7 is an enlarged, fragmentary, plan view of the corner on one of the shelves on the support in FIG. 3;

FIG. 8 is an elevation view of an upright on the support in FIG. 3;

FIG. 9 is a view as in FIG. 8 of an upright having a different length than the upright in FIG. 8;

FIG. 10 is a cross-sectional view of an upright, according to the present invention, having a variable length;

FIG. 11 is a schematic, side elevation view of a modified form of support, according to the present invention, and shown in an assembled state; and FIG. 12 is a view as in FIG. 11 with the support in a collapsed state.

DETAILED DESCRIPTION OF THE DRAWINGS

Figure 1:
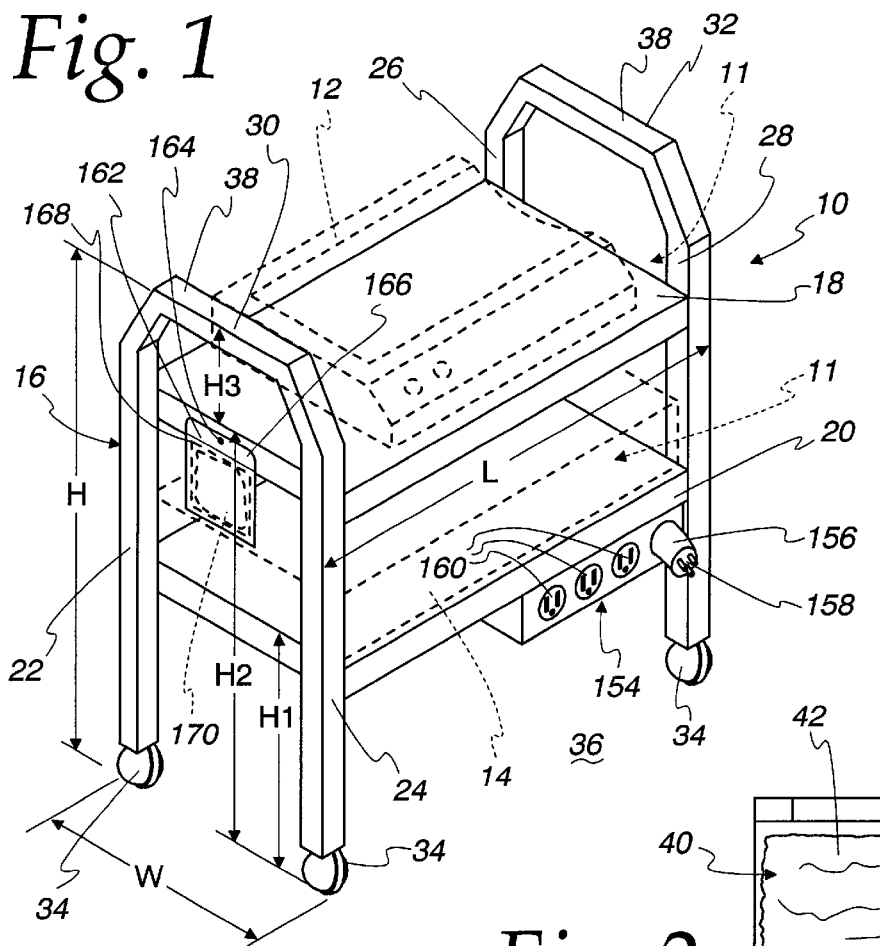
FIG. 1 is perspective view of a dialysis system, according to the present invention, including a self-contained dialysis unit in an operative position on a support.
Figure 2:
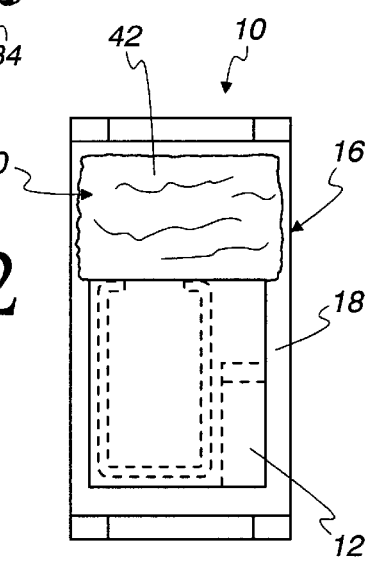
FIG. 2 is a plan view of the dialysis system in FIG. 1.
Figure 6:
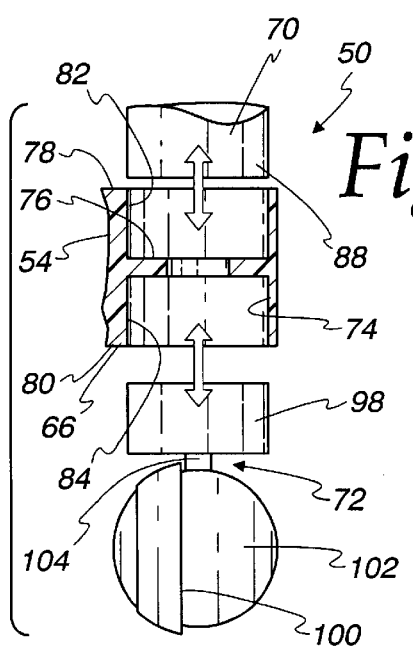
FIG. 6 is an enlarged, fragmentary, exploded, cross-sectional view of the connection between a shelf, an upright, and a wheel, taken along lines 6—6 in FIG. 3.

In FIGS. 1 and 2, one form of dialysis system, according to the present invention, is shown at 10. The system 10 includes a self-contained dialysis unit 11, which may be a continuous ambulatory peritoneal dialysis system (CAPD system), such as that currently offered by Baxter Health Care Corporation, and having as its principal components a control unit 12 and a fluid reservoir 14. The control unit 12 of the CAPD system currently offered by Baxter Health Care Corporation has a length on the order of 18.5 inches, a height on the order of 6.5 inches, and a width on the order of 14.5 inches.

The present invention is not concerned with the specific operation of the dialysis unit 11. It suffices to say that, in operation, the dialysis unit 11 requires that the control unit 12 and reservoir 14 be in relatively close proximity to each other and the patient.

The invention is directed to the combination of the dialysis unit 11 and a support 16 therefor, including an upper shelf 18 upon which the control unit 12 is supported and a lower shelf 20, upon which the reservoir 14 is supported. The shelves 18,20 are maintained in elevated, spaced relationship by corner uprights 22, 24, 26, 28. The uprights 22, 24 are joined at their top by a handle 30, with the uprights 26, 28 joined in like fashion by a handle 32.

Wheels 34 are provided, one each on the bottom of the uprights 22, 24, 26, 28. With the dialysis unit 11 placed in an operative position on the support 16, as shown in FIGS. 1 and 2, the patient is able to conveniently operate the dialysis unit, while at the same time rolling the support 16 over a subjacent surface 36. Either of the handles 30, 32 can be conveniently grasped by the user to facilitate rolling movement of the support 16. A foam rubber coating 38 may be provided on each of the handles 30, 32 to make the handles 30, 32 more comfortable to the grip.

The elements making up the support 16, including the uprights 22, 24, 26, 28, handles 30, 32, and shelves 18, 20, may be made from a lightweight material, such as plastic. These elements lend themselves to formation by a molding process. The lightweight construction is preferred to contribute to the ease of movement of the support 16 by the patient during a dialysis procedure. However, the invention contemplates formation of the support 16 by other materials, such as wood, metal, etc.

The support 16 is also made compact in size so that it can be conveniently maneuvered around a typical home. The support 16 shown has a length (L), a width (W), and a height (H). In one preferred form, H=34 inches, W=18 inches, and L=36 inches. Preferably, the length (L) does not exceed 4 feet, the height (H) does not exceed 4 feet, and the width (W) does not exceed 3 feet.

In the embodiment shown, the lower shelf 20 is spaced from the surface 36 a distance H1, which is approximately 14 inches. The upper shelf 18 is spaced from the surface 36 a distance H2, which is approximately 22½ inches. The handles 30, 32 project above the upper shelf 18 a distance H3, which is approximately 11½ inches.

The wheels 34 may be of any suitable construction. In one preferred form, a 2½ inch caster with a polypropylene wheel is utilized. Casters suitable for this purpose are commercially offered by several different manufacturers.

The above arrangement conveniently supports the dialysis unit 11 and provides a convenient access space 40 on the upper shelf 18 for the patient. In this case, a towel 42, or other suitable cover, can be laid across the upper shelf 18 immediately adjacent to the control unit 12 for the comfort and convenience of the patient.

In FIGS. 3, 4, and 6–9, an alternative embodiment of the inventive support is shown at 50. The support 50 is made to be collapsible to facilitate its transportation. The support 50 cooperates with the dialysis unit 11 in the same manner as does the support 10.

More particularly, the support 50 has upper and lower shelves 52, 54, respectively. The shelves 52, 54 are molded from plastic and may each be identical in construction. The exemplary shelf 54 has a continuous peripheral frame 56 with a lattice structure at 58 therewithin defined by mutually reinforcing longitudinally extending ribs 60 and transverse ribs 62. This construction provides a sturdy shelf 52, 54, yet one that is lightweight by reason of being made from plastic and by reason of the voids created by the lattice structure 58.

The shelf 54 has thickened corners 64, 66, 68 (three of four shown in FIG. 3) which provide rigid mounting bases for uprights 70 and wheel assemblies 72. The exemplary corner 66 has a through opening 74 with a dividing wall 76 midway between the top and bottom surfaces 78, 80 of the shelf 54 to thereby define an upwardly opening, cup-shaped receptacle 82 and a downwardly opening, cup-shaped receptacle 84.

Each of the upper and lower ends 86, 88 of the uprights 70 is designed to be frictionally retained within either of the receptacles 82, 84, and to be abuttable to the wall 76. With this arrangement, the user can assemble the support 50 by press fitting an upright 70 into each of the receptacles 82 on the lower shelf 54 and each of the receptacles 84 on the upper shelf 52.

Figure 5:
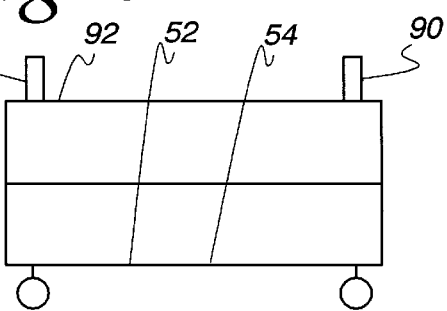
FIG. 5 is a schematic, side elevation view of a modified form of support, according to the invention, with one more shelf thereon than on the support shown in FIG. 3, and with the support in an assembled state.

If it is desired to add another shelf or to provide a pushing/pulling handle 90, an upright 70 can be pressed into each of the receptacles 82 in the upper shelf 52. The upper ends 86 of the uprights 70, projecting from the upper shelf 52, can then cooperate with another shelf 92, shown schematically in FIG. 5. Alternatively, the U-shaped handles 90 each attach to the upper ends 86 of a pair of the uprights 70.

Each handle 90 has downtuned ends 94, 96 which press fit to the upright ends 86. The ends 94, 96 and upright ends 86 fit one within the other and are frictionally maintained together.

To mobilize the support 50, the wheel assemblies 72 are pressed into the receptacles 84 on the lower shelf 54. Each wheel assembly 72 has an adapter 98 which provides a foundation for a wheel 100, which rotates relative to a support 102 carried by a stem 104 that projects into the adapter 98. The adapter 98 is frictionally held within the receptacle 84. The adapter 98 could alternatively be permanently fixed within the receptacle 84, with the stem 104 being press fit thereinto in a conventional manner.

With the inventive structure, the user can assemble the main structural elements of the support 50, consisting of the shelves 52, 54 and uprights 70, by a simple press fit operation. The support 50 can be disassembled by simply withdrawing the uprights 70 from the shelves 52, 54. The handles 90 can be friction fit and disassembled from the uprights 70 in a similar manner.

The support 50 can be placed in a collapsed state, shown in FIG. 4. In the collapsed state, the shelves 52, 54 are stacked and the uprights 70, handles 90, and wheel assembly 72 in turn stacked on or around the shelves 52, 54 in a compact manner.

Preferably, the perimeter volume of the support 50 in its assembled state is substantially larger than the perimeter volume of the support 50 in its collapsed state. The perimeter volume is the cubicle space bounded by three pairs of spaced, parallel planes which closely contain the support 50. For example, in FIG. 4, the perimeter volume of the collapsed support 50 would be the volume bounded by the space enclosed by a) a first plane that is flush with the flat bottom surface 106 of the lower shelf 54, b) a second plane parallel to the first plane that abuts the upwardmost extension of the stacked uprights 70, c) third and fourth parallel planes flush with the ends 108, 110 of the stacked shelves 52, 54, and d) fifth and sixth planes flush with the parallel sides 112, 114 of the stacked shelves 52, 54.

It is preferred that the perimeter volume of the collapsed support 50, including at least the shelves 52, 54 and uprights 70, and more preferably including the stacked shelves 52, 54, uprights 70, and the handles 90, be less than one-third the perimeter volume of the support 50 in its assembled state. More preferably, the perimeter volume of the collapsed support 50 is on the order of one-fifth the perimeter volume of the assembled support 50.

The height of the shelves 52, 54, and the spacing therebetween, can be easily changed by using uprights 70 with different lengths. In FIG. 8, an upright 70' is shown with a length greater than the upright 70. FIG. 9 shows an upright 70" with a length greater than the uprights 70, 70'. The assembly process with each of the uprights 70', 70" is the same as that for the upright 70.

To make the uprights universal in nature, an adjustable upright 120, according to the present invention, is used, as shown in FIG. 10. The upright 120 consists of first and second cooperating parts 122, 124 that are telescoped, one within the other. In this case, the upright part 122 has a reduced diameter portion 126 to fit within the upright part 124. A spring-loaded lug 128 on the part 122 can be selectively directed through openings 130, 132, 134 spaced lengthwise along the upright part 124 to thereby change the effective length of the upright 120. By simply pushing in upon the lug 128, the parts 122, 124 can be relatively repositioned. The upright 120 has ends that are frictionally press fit to the shelves 52, 54 and the handles 90 in the same manner as the uprights 70, 70', 70", previously described.

In FIGS. 11 and 12, a modified form of support, according to the present invention, is shown at 140. The support 140 includes upper and lower shelves 142, 144 that are joined by a plurality of link pairs, each including links 148, 150, with each link 148, 150 in turn having ends joined pivotably to one of the shelves 142, 144 and the other link in the pair 146. With this arrangement, the links 148, 150 can be aligned lengthwise, to produce a rigid support between the shelves 142, 144. By collapsing the link pairs 146 from the assembled position, the support 140 can be collapsed as shown in FIG. 12. This accounts for a significant volume reduction to facilitate transportation of the support 140.

For added convenience, a power distribution unit 154, shown in FIG. 1, can be incorporated. This unit 154 can be used on any of the embodiments described herein and may be permanently or releasably attached to any convenient part of the support 16. In the embodiment shown, the power distribution unit 154 is shown mounted to the underside of the shelf 20.

The power distribution unit 154 has a cord 156 with a male end fitting 158 to be plugged into a conventional 110 volt household receptacle. The cord 156 is retractable into the unit 154 for convenience and may be extendable up to 10–20 feet, as demand dictates. With the cord 156 plugged in, power is fed to a series of receptacles 160 into which the components of the dialysis unit 11 can be plugged. The power distribution unit 154 can be equipped with an amperage converter to be compatible with the power demands for the dialysis unit 11.

As another convenience to the user, an envelope-type holder 162 can be pelmanendy or releasably attached to the support 16, as by the use of a screw 164. In this case, the holder 162 is mounted to the upper shelf 18 for convenient access. The holder 162 has a backing wall 166 and a flap 168 which cooperatively define a receptacle, as for literature 170 related to the operation of the dialysis unit 11. The flap 168 can be drawn away from the backing wall 166 to facilitate access to the space therebetween for insertion and removal of the literature 170.

The inventive supports 16, 50, 140 provide a convenient, portable unit upon which a dialysis unit 11, such as a CAPD system, can be carried. The patient is given the freedom to perform the dialysis procedure while moving the supports 16, 50, 120. In the event that the patient wishes to carry out the dialysis procedure and another location, the supports 50, 120 can be conveniently collapsed to a significantly reduced volume and transported, as in the trunk or rear seat of an automobile. With the press fit arrangement of structural elements, the user can quickly reassemble the support 50, 120 at a new location. The inventive structure offers the patient an opportunity to enjoy more freedom during dialysis treatments and the freedom to carry out the procedure at any desired location.

The foregoing disclosure of specific embodiments is intended to be illustrative of the broad concepts comprehended by the invention.

I claim:

1. A method of facilitating peritoneal dialysis on a patient, said method comprising the steps of:

providing a support comprising at least one shelf, at least one upright for maintaining the at least one shelf in an elevated position above a subjacent surface upon which the support is placed, and at least one wheel;

placing a self-contained peritoneal dialysis unit on the at least one shelf;

conducting peritoneal dialysis on the patient using the self-contained peritoneal dialysis unit with the self-contained peritoneal dialysis unit on the at least one shelf; and moving the support through the at least one wheel acting against a subjacent surface upon which the support is placed together with the patient from a first location to a second location as peritoneal dialysis is performed on the patient.

2. A method of having peritoneal dialysis performed using a self-contained peritoneal dialysis unit on a portable support which support comprises at least one wheel to be placed against a subjacent surface, said method comprising the step of:

moving as a patient from a first location to a second location; and moving the set-contained peritoneal dialysis unit from the first location to the second location by movement of the at it one wheel against the subjacent surface while peritoneal dialysis is being performed on the patient is the patient moves from the first location to the second location.

3. The method of having peritoneal dialysis performed according to claim 2 wherein the portable support comprises a plurality of assembled elements and further comprising the steps of separating the self-contained peritoneal dialysis unit from the portable support, disassembling the plurality of elements, transporting the disassembled elements to a third location, and at the third location reassembling the plurality of elements and replacing the self-contained peritoneal dialysis unit on the portable support.

4. The method of having peritoneal dialysis performed according to claim 3 further comprising the steps of having peritoneal dialysis performed by the patient at the third location.

* * * * *